(12) United States Patent
Lau et al.

(10) Patent No.: US 8,748,499 B2
(45) Date of Patent: Jun. 10, 2014

(54) COLLAGEN DISPERSION AND METHOD OF PRODUCING SAME

(75) Inventors: Francis C. Lau, Vallejo, CA (US); Massood Moshrefi, Benicia, CA (US)

(73) Assignee: Interhealth Nutraceuticals, Inc., Benicia, CA (US)

( * ) Notice: Subject to any disclaimer, the term of this patent is extended or adjusted under 35 U.S.C. 154(b) by 274 days.

(21) Appl. No.: 12/757,698

(22) Filed: Apr. 9, 2010

(65) Prior Publication Data

US 2010/0303898 A1    Dec. 2, 2010

Related U.S. Application Data

(60) Provisional application No. 61/168,406, filed on Apr. 10, 2009.

(51) Int. Cl.
*A01N 25/00* (2006.01)
*A61K 9/00* (2006.01)

(52) U.S. Cl.
USPC .......... 514/773; 424/400; 424/401; 424/439; 424/450

(58) Field of Classification Search
USPC ......................................... 424/400; 514/773
See application file for complete search history.

(56) References Cited

U.S. PATENT DOCUMENTS

| | | | |
|---|---|---|---|
| 3,691,281 A | | 9/1972 | Battista |
| 5,153,067 A | | 10/1992 | Yoshida et al. |
| 5,645,851 A | * | 7/1997 | Moore .......................... 424/439 |
| 6,162,787 A | * | 12/2000 | Sorgente et al. ............. 514/16.8 |
| 6,749,868 B1 | | 6/2004 | Desai et al. |
| 2008/0260843 A1 | | 10/2008 | Ooya et al. |

OTHER PUBLICATIONS

International Search Report and Written Opinion for International Application No. PCT/US10/30571 dated Jun. 28, 2010.

* cited by examiner

*Primary Examiner* — Frederick Krass
*Assistant Examiner* — Dennis J Parad
(74) *Attorney, Agent, or Firm* — Marshall, Gerstein & Borun LLP

(57) ABSTRACT

A stable dispersion of insoluble collagen is provided by a microfluidization process. The dispersions of insoluble collagen protein remain in stable suspension under long term storage conditions, with minimal or no settling or precipitation. More specifically the invention provides a stable dispersion of insoluble collagen comprising collagen particles wherein 50% by volume of said particles are less than 30 micrometers in width. These dispersions provide collagen in an aqueous form, which enables ease of incorporation into food and beverages and ease of administration to people or other mammals in need of collagen.

10 Claims, 1 Drawing Sheet

COLLAGEN DISPERSION AND METHOD OF PRODUCING SAME

Figure 1:
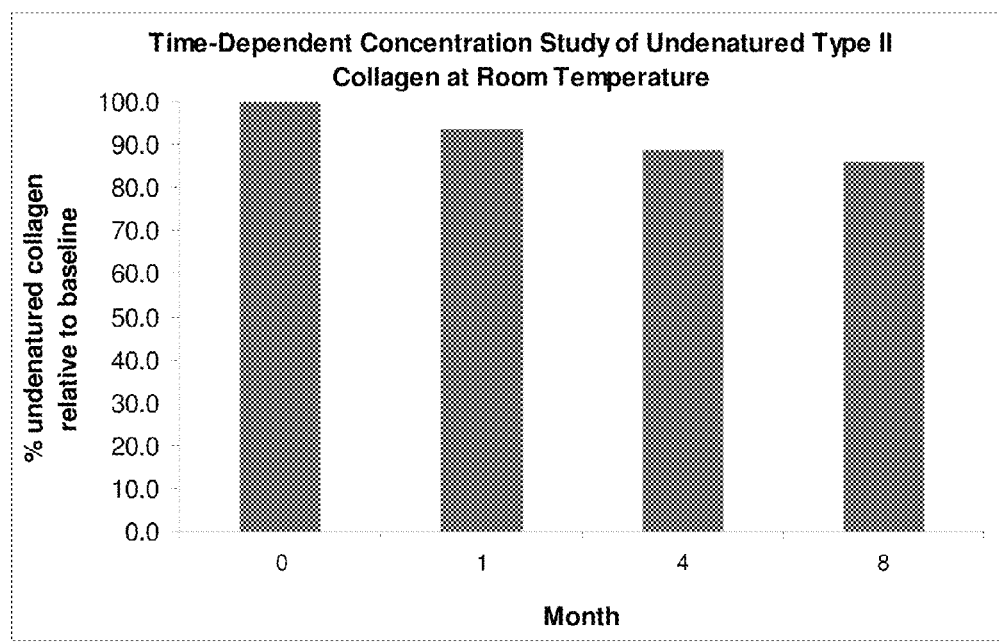

Benefit of U.S. Provisional Application No. 61/168,406, filed Apr. 10, 2009, the disclosure of which is incorporated by reference in its entirety, is claimed.

FIELD OF THE INVENTION

The present invention relates to collagen protein compositions and particularly to those for human or animal consumption.

Undenatured collagen products are particularly preferred for various uses such as treatment of the symptoms of arthritis.

BACKGROUND

Of interest to the present invention are the disclosures of Moore, U.S. Pat. Nos. 5,529,786; 5,637,321; 5,645,851 and 5,750,144 which disclose methods for preparing water-insoluble, undenatured type II collagen compositions including those separated from non-type II collagen containing tissue. The patents also disclose the use of such water-insoluble undenatured type II collagen for the treatment of arthritis symptoms including the symptoms of rheumatoid arthritis and osteoarthritis. In contrast to water-soluble highly purified type II procollagen, the use of undenatured insoluble type II collagen avoids the need for complex purification. Small doses of undenatured type II collagen deactivate killer T-cell attack of joint cartilage in humans and collagen improves arthritic symptoms in older women. See Bagchi et al., Effects of Orally Administered Undenatured Type II Collagen Against Arthritic Inflammatory Diseases: a Mechanistic Exploration, International Journal of Clinical Pharmacology Research 22: 101-110 2002 and D'Altilio et al., Therapeutic Efficacy and Safety of Undenatured Type II Collagen Singly or in Combination with Glucosamine and Chondroitin in Arthritic Dogs, Toxicology Mechanisms and Methods 17: 189-196 2007. Recently, a human clinical study was conducted in approximately 52 osteoarthritic subjects. Subjects (n=26) treated with undenatured type II collagen exhibited marked improvements without any significant adverse events. Furthermore, this study demonstrated the superior efficacy of undenatured type II collagen in comparison to Glucosamine+Chondroitin treatment (n=26) as measured by WOMAC, VAS and Lequesne osteoarthritis assessment scores. See Gupta et al., Safety and Therapeutic Efficacy of Undenatured Type II Collagen (UC-II) in Horses, Soc. Toxicology, Abstract of the 46th Annual Meeting (2007) and Bagchi et al., Beneficial effects of oral administration of undenatured type II collagen on osteoarthritis: a human clinical trial, American College of Nutrition: abs, October 2008; See also Gupta et al., Pain Reduction Measured by Ground Force Plate Arthritic Dogs Treated with Type-II Collagen, Soc. Toxicology, Abstract of the 48th Annual Meeting (2009).

While solid tablets and capsules have been used for the delivery of collagen there remains a desire for other delivery modes. In particular it is desired that subjects be able to consume collagen as part of a food or beverage, particularly for those having difficulty consuming pills or capsules. One particularly preferred type of collagen for human and veterinary consumption is water-insoluble collagen which by its very nature is not well-suited for formulation into a beverage because it will not remain in suspension to form a stable dispersion. Accordingly, there remains a desire for methods of producing stable aqueous dispersions of collagen that may be incorporated into nutraceutical beverages and foods to promote joint health in osteoarthritis sufferers as well as be used in cosmetics and the like.

Also of interest to the present invention are high pressure mixer/reactor devices such as Microfluidizer® materials processors available from Microfluidics International Corp. (Newton, Mass. and those described in Thumm et al., U.S. Pat. No. 6,221,332 which discloses the pressurization of individual reactant streams to from 8,000 to 50,000 psi and the propulsion of reactants at velocities of up to 250 meters per second.

SUMMARY OF THE INVENTION

The present invention is directed to methods of producing dispersions of insoluble collagen protein which remain in stable suspension under long term storage conditions. More specifically the invention provides a stable dispersion of insoluble collagen comprising collagen particles wherein 50% by volume of said particles are less than 30 micrometers in width. As used herein, a stable dispersion refers to a dispersion of collagen that remains in dispersion, without precipitating or settling, for at least 30 days at room temperature. The collagen particles in the dispersion are preferably 50% by volume less than 20 micrometers, less than 10 micrometers, less than 8 micrometers, or less than 5 micrometers in width. As used herein, particles can refer to individual particles of collagen or agglomerated particles of collagen, where one or more particles of individual particles of collagen stick to one another. An accurate method for characterizing particles by size includes the use of a particle size analyzer, for example, a Microtrac particle size analyzer.

Preferred dispersions are characterized by being stable such that the collagen particles are capable of remaining in suspension for at least 30 days at room temperature, and preferably remaining in suspension for greater than 4 months, 8 months, one year or longer, such as two years. The dispersions preferably comprise undenatured type II collagen. A particularly useful type II collagen is undenatured type II collagen available commercially as UC-II® available from InterHealth Nutraceuticals (Benicia, Calif.).

The dispersions also remain substantially undenatured, as compared to the initial concentration of undenatured collagen. The amount of undenatured collagen can be measured by detecting the presence of biologically active epitopes on the undenatured type II collagen using an Enzyme Linked Immunosorbent Assay (ELISA). The presence of these epitopes correlate to the presence of undenatured type II collagen. For example, greater than 90% of the collagen in the dispersion preferably remains undenatured for one month. Preferably, greater than 88% of the collagen in the dispersion remains undenatured for four months. Greater than 85% of the collagen in the dispersion preferably remains undenatured for eight months. The dispersion may also be tested for the presence of microbial growth.

Also provided are methods of producing such stable dispersions of insoluble collagen comprising the steps of: mixing dried powdered cartilage material with water; processing the formulation in a microfluidizer processor; and cooling the material immediately after it passed through the microfluidizer processor. The microfluidizer processor preferably comprises multiple interaction chambers. The material is preferably cooled in an ice water bath.

According to one preferred embodiment the microfluidizer unit is an M-110S Microfluidizer® processor (Microfluidics Corp., Newton Mass.) using a G10Z (87 μm) interaction chamber or a H30Z (200 μm) interaction chamber at a pressure from 10,000 to 25,000 psi, with 23,000 psi being preferred, for from one to five passes. Preferably, the material is processed in the microfluidizer unit for four or five passes.

The stable collagen dispersions may be used in a variety of end uses including in foods and beverages, as a sublingual delivery system and also in liposomes for delivery of a variety of compositions including, but not limited to cosmetics.

DESCRIPTION OF THE DRAWING FIGURES

Figure 2:
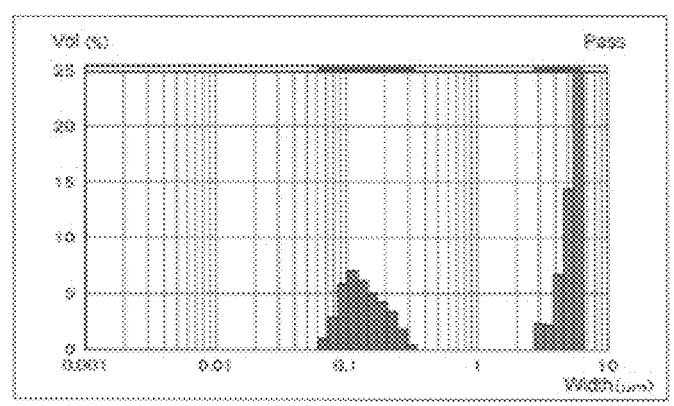

For a more complete understanding of the disclosure, reference should be made to the following detailed description and accompanying drawings wherein:

FIG. 1 is a chart showing retention of the undenatured from of type II collagen in a dispersion stored at room temperature where the concentration was measured initially and at 1, 4, and 8 months; and, FIG. 2 is a distribution of particle sizes in a dispersion.

DETAILED DESCRIPTION

The present invention is directed to methods of producing dispersions of insoluble collagen protein which remain in stable suspension under long term storage conditions, with minimal or no precipitation or settling. According to one aspect of the invention, collagen is subjected to microfluidization processing to decrease the particle size of the dispersions. The resulting processed material has an increased viscosity and a fluffy consistency compared with unprocessed material which immediately settles out of solution. These dispersions provide collagen in an aqueous form, which enables ease of incorporation into food and beverages and ease of administration to people or other mammals in need of collagen.

The dispersion of the collagen results in a more stable product. The dispersions are capable of remaining in suspension for at least 30 days at room temperature, and preferably remaining in suspension up to 4 months, 8 months, one year or longer, such as two years. The dispersions preferably comprise undenatured type II collagen.

In addition, these dispersions can be stored at room temperature, with minimal denaturation. For example, at room temperature, the dispersion can preferably be stored for one month with greater than 50%, greater than 60%, greater than 70%, greater than 80%, greater than 90%, or greater than 93% of the initial concentration of the undenatured type II collagen remaining undenatured. At four months, the dispersion can preferably be stored at room temperature with greater than 50%, greater than 60%, greater than 70%, greater than 80%, greater than 85%, or greater than 88% of the initial concentration of the undenatured type II collagen remaining undenatured. At eight months, the dispersion can preferably be stored at room temperature with greater than 50%, greater than 60%, greater than 70%, greater than 80%, or greater than 85% of the initial concentration of the undenatured type II collagen remaining undenatured. The percent collagen that remains undenatured can be assayed by ELISA to confirm the presence of epitopes on the dispersed undenatured type II collagen, which indicates the collagen is undenatured. Useful ELISA kits include type II collagen detection kits and are manufactured by Chondrex, Inc. (Redmond, Wash.). It is believed that as the collagen becomes denatured, the epitopes measured by ELISA decrease. Thus, the dispersions provide a stable product, i.e., the collagen does not settle or precipitate out of suspension. Further, the dispersions provide a high rate of retention of the undenatured form of type II collagen.

Any type and species of collagen may be subjected to the processing and used according to the invention. Both denatured and undenatured collagen may be used but undenatured collagen is particularly preferred for many applications. Collagen may be derived from any of a variety of animal species including humans, and non-human mammalian species including bovine and porcine species. In addition, collagen derived from avian species such as chickens is in many cases preferred because of its freedom from many disease pathogens associated with human and bovine species including BSE.

Suitable microfluidizers for use according to the invention include those produced by Microfluidics Corp., Newton Mass. such as M-110S, M-110Y, M110EH or M700 Microfluidizer® processors including the G10Z (87 µm) or H30Z (200 µm) interaction chambers. The microfluidizer devices comprise pumps to supply pressure to a product stream which is driven through fixed geometry microchannels within an interaction chamber. Suitable processing pressures range between 10,000 psi and 30,000 psi with pressures of 20,000 psi to 25,000 psi being preferred. The product is accelerated to high velocities creating extremely high shear rates within the product stream. The shear then operates to reduce collage particle sizes within the mixture. The dispersion is preferably cooled after micronization to reduce denaturation caused by the heat from the micronization process. A preferred method of cooling is using an ice water bath.

The microfluidizers preferably produce dispersions of undenatured type II collagen with 50% of the particles by volume at a size in a range of about 40 micrometers to about 4 micrometers in width. For example, the dispersions preferably have 50% of the particles by volume at a size less than 75 micrometers, less than 65 micrometers, less than 40 micrometers, less than 30 micrometers, less than 20 micrometers, less than 10 micrometers, less than 9 micrometers, less than 8 micrometers, less than 7 micrometers, less than 6 micrometers, less than 5 micrometers, and less than 4 micrometers in width. As used herein, particles can refer to individual particles of collagen or agglomerated particles of collagen, where one or more particles of individual particles of collagen stick to one another.

The protein of the dispersed undenatured type II collagen has not been altered substantially by the micronization process. The undenatured type II collagen retains biological activity after the microfluidization process.

The particles are preferably characterized by a particle size analyzer, such as a Microtrac particle size analyzer. In addition, the particles can be quantified in the flow cell of a static light scattering instrument, such as a Horiba® LA-910 Static Light Scattering instrument, and visualized by microscopic analysis, such as an Olympus BH-2 optical microscope, after 60-second sonication.

The collagen compositions may be passed a single time through the processors or more preferably may be cycled through multiple passes with from 3 to 5 passes being preferred. For example, the collagen compositions may be passed one time, two times, three times, four times, or five times through the processor to produce the dispersion.

Another method for producing stable dispersions includes: mixing collagen with water to form a mixture; microfluidizing the mixture to form a dispersion; and cooling the dispersion after microfluidizing. Microfluidizing is preferably performed in a microfluidizer processor. Microfluidizing can preferably include passing the mixture multiple times through the microfluidizer processor, for example, one to five times. Cooling is preferably performed immediately after the mixture has been microfluidized.

EXAMPLES

Example 1

According to one example a commercially available microfluidizer unit (M-110S) equipped with a G10Z (87 μm) interaction chamber or with a H30Z (200 μm) interaction chamber was used to treat a commercially available ground undenatured chicken sternum cartilage (UC-II® UC250) available from InterHealth Nutraceuticals (Benicia, Calif.) which comprises 25% undenatured type-II collagen in powder form. The UC-II® cartilage was produced according to the methods described in Moore, U.S. Pat. Nos. 5,529,786; 5,637,321; 5,645,851 and 5,750,144 wherein sternum cartilage harvested from 4-6 week old chickens was harvested and cleaned with sodium hypochlorite (NaOCl) sanitizer solution by soaking for a minimum of 12 hours. The particle size of the cartilage was reduced using a Hobart grinder and the material was treated with a 30% KCl aqueous solution. The cartilage material was then dried in a rotary drum drier for 1.5 to 4 days at a temperature of less than 104° F. to produce a dried material.

The dried powdered cartilage material was combined with water at a rate of 10 grams powder (containing 2.5 grams of undenatured type II collagen) per 150 mL water (6.25 wt. percent). The combination was shaken vigorously by hand for 5 minutes prior to processing in a microfluidizer processor. The formulations were then processed in an M-110S Microfluidizer® processor (Microfluidics Corp., Newton Mass.) using the G10Z (87 μm) interaction chamber or with a H30Z (200 μm) interaction chambers at varied pressures for varied number of passes. An ice water bath was used to cool the material immediately after it passed through the interaction chamber.

The resulting products were analyzed using a Horiba® LA-910 static light scattering instrument. During the measurement, the material was sonicated for 60 seconds in the flow cell of the instrument. During the measurement, the material was sonicated for 60 seconds in the flow cell of the Horiba® LA-910 device. The processed material was also analyzed using the Olympus® BH-2 optical microscope with the results presented in Table 1 below:

TABLE 1

PARTICLE SIZING DATA

| Process Conditions | Number of Passes | Particle Size (microns) | | | |
|---|---|---|---|---|---|
| | | *d10 | d50 | d95 | Mean |
| Unprocessed Collagen | n/a | 14.517 | 73.403 | 265.808 | 96.287 |
| Test #1: M-110S; 23,000 psi; G10Z (87 μm); | 1 Pass | 16.428 | 55.380 | 209.412 | 75.110 |
| | 3 Passes | 11.833 | 35.937 | 115.073 | 44.921 |
| | 5 Passes | 9.920 | 31.052 | 86.200 | 36.552 |
| Test #2: M-110S; 10,000 psi; H30Z (200 μm); | 1 Pass | 20.185 | 98.875 | 441.537 | 144.207 |
| | 3 Passes | 18.699 | 70.651 | 257.107 | 93.820 |
| | 5 Passes | 13.474 | 63.695 | 417.104 | 112.061 |
| Test #3: M-110S; 15,000 psi; H30Z (200 μm); | 1 Pass | 20.190 | 94.060 | 341.372 | 124.352 |

*dX denotes X% of the material by volume is smaller than the particle size specified. For example, d50 for Test #1, 5 passes = 31.052 which means 50% of the particles by volume is smaller than 31.052 micron.

Microscopic analysis indicates that the particle size of the dispersions was reduced by treatment with the microfluidizer devices. Particle size data reported in Table 1 shows a certain amount of particle size reduction between each pass, however, the particle size data does not correlate with the microscopic analysis. This miscorrelation may be due to the accuracy of microscopic analysis when measuring particles, the majority of which may be too small to detect. Thus, these experiments are likely skewed to measure only very large particles and miss detection of smaller particles. Polysorbate-80 (Tween-80) surfactant was used to try to achieve more representative particle size distributions but was not effective in doing so. A particle size analysis using a particle size analyzer would be more accurate in characterizing the size of the particles. The next example details a method of characterizing particles using a particle size analyzer.

Example 2

A commercially available microfluidizer unit (M-110S Microfluidizer® processor) equipped with a G10Z (87 μm) interaction chamber or with a H30Z (200 μm) interaction chamber was used to treat a mixture of 10 grams of UC-II® (described above) in 150 mL of water. The mixture was micronized with four passes in the unit to form a dispersion.

The dispersion remained stable, i.e., without settling, for 30 days, 4 months, and 8 months at room temperature. The concentration of undenatured type II collagen in the dispersions was also tested initially and at 1, 4, and 8 months. The dispersion was tested by ELISA to confirm the presence of epitopes on the dispersed collagen, which indicates that the collagen is undenatured. The results are shown in FIG. 1 and Table 2, below.

TABLE 2

| Duration (months) | Concentration of undenatured type II collagen (mg/mL) | % undenatured collagen relative to baseline |
|---|---|---|
| 0 | 13.62 | 100 |
| 1 | 12.77 | 93.8 |
| 4 | 12.08 | 88.7 |
| 8 | 11.71 | 86 |

The particles in the dispersion were tested on a Microtrac particle size analyzer. The results revealed that the average particle size was 4.79 micrometers at the $50^{th}$ percentile. The pH of the dispersion was 4.75. FIG. 2 is a particle size analysis of the dispersion, showing two peaks. The first peak corresponds to individual particles. The second peak corresponds to agglomerated particles, where one or more individual particles of collagen stick to each other. Table 3, below, details the particle sizes of the dispersion as a percentage of the particles with a certain width or less, as characterized by the Microtrac particle size analyzer.

TABLE 3

| Percentage of particles | Size (μm) |
|---|---|
| 10 | 0.1035 |
| 20 | 0.1335 |
| 30 | 0.1887 |
| 40 | 3.4342 |
| 50 | 4.7933 |
| 60 | 5.4001 |
| 70 | 5.6942 |
| 80 | 5.9392 |
| 90 | 6.1875 |
| 95 | 6.3429 |

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A stable liquid dispersion of insoluble collagen comprising collagen particles wherein 50% by volume of said particles are from 40 microns to 4 microns in width and wherein the collagen is undenatured type II collagen, the particles are capable of remaining in suspension for at least four months at room temperature and greater than 87% of the collagen in the dispersion remains undenatured for four months and wherein the stable dispersion is produced according to the method comprising the steps of mixing dried powdered cartilage material with water;
processing the resulting formulation in a microfluidizer processor in more than one pass; and
cooling the material immediately after it passes through the microfluidizer processor.

2. The stable dispersion of claim 1, wherein the particles are capable of remaining in suspension for at least one year at room temperature.

3. The stable dispersion of claim 1, wherein greater than 85% of the collagen in the dispersion is capable of remaining undenatured for eight months.

4. A method of producing a stable liquid dispersion of insoluble collagen comprising collagen particles, said method comprising the steps of mixing dried powdered cartilage material with water;
processing the resulting formulation in a microfluidizer processor; and
cooling the material immediately after it passes through the microfluidizer processor; wherein 50% by volume of said particles are from 40 microns to 4 microns in width and wherein the collagen is undenatured type II collagen, the particles are capable of remaining in suspension for at least four months at room temperature and greater than 87% of the collagen in the dispersion remains undenatured for four months.

5. The method of 4 wherein the microfluidizer is an M-110S microfluidizer processor using a G10Z (87 μm) interaction chamber or a H30Z (200 μm) interaction chamber at a pressure from 10,000 to 25,000 psi from one to five passes.

6. The method of 5 wherein the pressure is 23,000 psi and five passes are used.

7. A food comprising the stable dispersion of insoluble collagen of claim 1.

8. A beverage comprising the stable dispersion of insoluble collagen of claim 1.

9. A liposome for cosmetics comprising the stable dispersion of insoluble collagen of claim 1.

10. A sublingual delivery system comprising a stable dispersion of insoluble collagen of claim 1.

* * * * *

UNITED STATES PATENT AND TRADEMARK OFFICE
CERTIFICATE OF CORRECTION

PATENT NO.       : 8,748,499 B2                                      Page 1 of 1
APPLICATION NO.  : 12/757698
DATED            : June 10, 2014
INVENTOR(S)      : Lau et al.

It is certified that error appears in the above-identified patent and that said Letters Patent is hereby corrected as shown below:

In the Claims:

At Column 7, line 13, "steps of" should be -- steps of: --.

At Column 7, line 27, "steps of" should be -- steps of: --.

At Column 8, line 12, "of 4" should be -- of claim 4 --.

At Column 8, line 17, "of 5" should be -- of claim 5 --.

Signed and Sealed this
Twentieth Day of October, 2015

Michelle K. Lee
*Director of the United States Patent and Trademark Office*